United States Patent
Nordstrom et al.

(10) Patent No.: US 11,691,034 B2
(45) Date of Patent: Jul. 4, 2023

(54) METHODS FOR STRENGTHENING AND REPAIRING NAILS USING CURABLE COMPOSITIONS

(71) Applicants: Famous Names LLC, Las Vegas, NV (US); Esschem, Linwood, PA (US)

(72) Inventors: Jim Nordstrom, Las Vegas, NV (US); Linda Nordstrom, Las Vegas, NV (US); Susan Sheariss, Swedesboro, NJ (US)

(73) Assignees: Famous Names, LLC, Las Vegas, NV (US); Esschem, Linwood, PA (US)

( * ) Notice: Subject to any disclaimer, the term of this patent is extended or adjusted under 35 U.S.C. 154(b) by 523 days.

(21) Appl. No.: 16/400,830

(22) Filed: May 1, 2019

(65) Prior Publication Data
US 2019/0255364 A1    Aug. 22, 2019

Related U.S. Application Data

(62) Division of application No. 14/209,063, filed on Mar. 13, 2014, now abandoned.

(60) Provisional application No. 61/783,135, filed on Mar. 14, 2013.

(51) Int. Cl.
| | |
|---|---|
| *A61Q 3/02* | (2006.01) |
| *A61K 8/37* | (2006.01) |
| *A61K 8/92* | (2006.01) |
| *A61Q 3/00* | (2006.01) |

(52) U.S. Cl.
CPC ............... *A61Q 3/02* (2013.01); *A61K 8/375* (2013.01); *A61K 8/922* (2013.01); *A61K 2800/81* (2013.01); *A61K 2800/95* (2013.01); *A61Q 3/00* (2013.01)

(58) Field of Classification Search
None
See application file for complete search history.

(56) References Cited

U.S. PATENT DOCUMENTS

| | | | |
|---|---|---|---|
| 5,681,550 A | 10/1997 | Rubino et al. | |
| 6,015,549 A | 1/2000 | Cowperthwaite et al. | |
| 6,244,274 B1 | 6/2001 | Sirdesai et al. | |
| 6,401,724 B1 | 6/2002 | Sawyer | |
| 6,818,207 B1 | 11/2004 | Schoon et al. | |
| 9,504,856 B2 | 11/2016 | Chodorowski-Kimmes et al. | |
| 2012/0118314 A1* | 5/2012 | Haile | A45D 29/12 132/200 |
| 2013/0034512 A1 | 2/2013 | Kozacheck et al. | |

FOREIGN PATENT DOCUMENTS

| | | |
|---|---|---|
| CN | 102429834 A | 5/2012 |
| CN | 103002867 A | 3/2013 |
| GB | 2452566 A | 3/2009 |
| RU | 2432151 C2 | 10/2011 |

OTHER PUBLICATIONS

Chinese Office Action for Chinese Application No. 201480027555.3, dated Feb. 3, 2020, with translation, 8 pages.
European Communication pursuant to Article 94(3) for European Application No. 14 770 741.8. dated Mar. 11, 2021, 9 pages.
Chinese Office Action for Chinese Application No. 201480027555.3, dated Sep. 30, 2017, with English translation, 19 pages.
Chinese Office Action for Chinese Application No. 201480027555.3, dated Jun. 15, 2018, with English translation, 13 pages.
Database GNPD [Online], Mintel; Oct. 31, 2011, "Soak Off UV Color Gel" XP002761964, 4 pages.
Database GNPD [Online], Mintel; Sep. 30, 2011, "UV Color Coat Nail Color", XP002761965, 4 pages.
Database GNPD [Online], Mintel; Feb. 28, 2013, "Color Gel Polish" XP002761966, 3 pages.
Database GNPD [Online], Mintel; Sep. 30, 2011, "Mini Soak Off Gel Polish" XP002761967, 3 pages.
Extended European Search Report dated Oct. 25, 2016 for European Application No. 14770741.8, 9 pages.
International Preliminary Report on Patentability on Application No. PCT/US2014/027262, dated Sep. 15, 2015, 7 pages.
International Search Report and Written Opinion for International Application No. PCT/US2014/027262, dated Sep. 15, 2015, 8 pages.
Record of the Interview for Russian Application No. 2015140712/15, dated Jul. 10, 2018, with English translation, 11 pages.
Russian Office Action for Russian Application No. 2015140712/15, dated Jun. 29, 2017, with English translation, 13 pages.
Russian Office Action for Russian Application No. 2015140712/15, dated Nov. 17, 2017, with English translation, 8 pages.
Communication pursuant to Article 94(3) EPC for European Application No. 14770741.8, dated Jun. 17, 2019, 6 pages.
Chinese Office Action for Chinese Application No. 201480027555.3, dated Jul. 10, 2019 with translation, 7 pages.
Communication pursuant to Article 94(3) EPC for European Application No. 14 770 741.8, dated Apr. 3, 2020, 9 pages.
Communication pursuant to Article 94(3) EPC for European Application No. 14 770 741.8, dated Jun. 21, 2022, 6 pages.

* cited by examiner

*Primary Examiner* — Nicole P Babson
(74) *Attorney, Agent, or Firm* — RatnerPrestia

(57) ABSTRACT

The present disclosure relates to a curable nail strengthening composition comprising a polymerizable material, at least one penetrating agent, and at least one curing agent. The strengthening composition penetrates the nail and is cured within the nail plate without cross-linking the nail proteins. Methods for strengthening and repairing nails are also disclosed.

14 Claims, No Drawings

METHODS FOR STRENGTHENING AND REPAIRING NAILS USING CURABLE COMPOSITIONS

CROSS-REFERENCE TO RELATED APPLICATIONS

This application is a division of U.S. application Ser. No. 14/209,063, filed Mar. 13, 2014, which claims priority of U.S. Provisional Patent Application Ser. No. 61/783,135, filed Mar. 14, 2013, the disclosures of each of which are incorporated herein by reference in their entirety for all purposes.

FIELD OF INVENTION

The present invention relates to curable compositions for structurally improving and reinforcing nail plates and methods for strengthening, improving toughness, durability, appearance and for repairing damaged nail plates, as well as to protect and support nail plates so they can grow and lengthen naturally.

BACKGROUND OF THE INVENTION

Natural nail plates, particularly the fingernails and toenails of humans, are comprised of multiple layers of translucent cells that are created within the nail matrix at the base or root of the nail plate and slowly transported toward the end of the fingertip, with the entire journey usually taking 4-6 months for fingernails and up to one year for toenails. Each nail plate cell contains keratin, a fibrous structural protein also found in hair and skin, as well as animal hooves and horns. The keratin naturally imparts structure, toughness, durability and flexibility to the nail plates, which ensures resistance to cracking, chipping, breaking and tearing.

Nail plates can become damaged during everyday activity through exposure to harsh or corrosive chemicals, overexposure to water, mechanical damage created from overly aggressive and improperly performed manicures or artificial nail application/removal procedures, over application/incorrect use of certain types of nail treatments/hardeners or due to infection or illness. Some people may also inherently have or develop thin/weak nail plates which easily tear, break or peel. The strength and durability of nail plates also normally decreases with advancing age. Damaged or weakened nail plates may be more susceptible to infection, excessive staining/discoloration or further continued damage. Also, as a result of advancing age, nail plates often develop grooves of varying depths which run the length of the natural nail plate. These grooves, often incorrectly perceived as ridges, can serve as weak points in the nail plate and act as seeds for initiating longitudinal splits or cracks which can develop in the plate as a result of the significant plate thinning in these grooved areas.

Increasing or restoring the nail plate's inherent toughness provides increased durability which allows the nail plate to better endure impacts and to resist externally applied physical forces in the form of everyday stresses, strains, etc. Toughness is a physical property achieved by a proper balance of strength and flexibility. Nail plates that are overly strong or hard can lose flexibility which can result in a loss of toughness and increased brittleness, cracking and/or breaking or may lead to damage to the underlying nail bed. Nails plates that are too weak do not have sufficient toughness often because they are overly flexible, which results in tearing, fracturing, as well, increased potential for nail bed damage.

Most attempts to improve or restore the durability of the nail plate focus on either (a) coating the plates' surface with the thick protective ultraviolet (UV) or thermally polymerizable surface layer or (b) application and absorption of natural oils which diffuse into the upper layers to plasticize overly rigid nail plates which increases flexibility and can result in increased toughness of nail plates that are overly rigid or (c) by increased hardening of the nail plates' surface by introducing additional cross-links between keratin proteins which results in a reduction of flexibility and increases strength, as well as increases scratch and indentation resistance.

The currently available strengthening compositions rely on coating the surface of the nail with polymerizable mixtures that form internal cross-links and tightly adhere to the plate's surface to substantially thicken the plate, adding the strength of the protective coating to that of the nail plate. Polymerizable surface coatings can also fill and reinforce longitudinal grooves which appear in the nail plate, which are typically seen with advancing age. The polymerizable surface coatings may also help prevent the longitudinal grooves from becoming cracks or splits in the nail plate. These compositions do not provide cross-linking within the keratin fibrils inside the cells of the nail plate, but instead, internal cross-linking creates greater cohesion and durability within the coating on the surface of the nail plate. These compositions, while improving the strength of the overall nail plate and protecting its surface from external damaging elements, do not improve flexibility of the plate. Also, necessary periodic removal and subsequent repeated application of the polymerizable coating often results in plate roughening, thinning, weakening and increased cracking, splitting and/or delaminating (peeling) of the upper layers of the nail plate from the bulk of the nail plate. Therefore, these coatings can increase damage to the nail plate in the process of protecting it and therefore aren't always useful or desirable, especially for thin, weak nail plates.

Three currently available types of nail plate hardening compositions are commonly used. The most widely used plate hardening composition is based on methylene glycol (also referred to as formaldehyde or formalin), which is the product formed when formaldehyde gas reacts with water. A typical 1% formaldehyde nail hardener would contain 1.6% methylene glycol and 0.0013% formaldehyde. The methylene glycol solution slightly penetrates the nail plate surface and over time, typically 4-5 days, will cross-link with the keratin present in the nail plate. This is due to the inherently slow reaction times of methylene glycol with keratin protein. Eventually, these reactions result in a permanent surface hardening, which provides increased scratch and indentation resistance, but produces a significantly less flexible nail plate that becomes increasingly rigid. Continued use of methylene glycol hardening compositions over time continually adds additional cross-linking to the keratin proteins which eventually leads to nail plate over-hardening and results in embrittlement and eventually breakage, thereby defeating the original purpose for using a nail hardener compositions. These types of nail hardeners provide useful benefits only for overly flexible nail plates and provide little to no positive benefits to other types of nail plates. These hardeners are detrimental for use on already brittle nail plates, or those with surface damage which increases porosity, speeding absorption to cause even faster nail plate embrittlement, splitting, chipping, cracking and surface delamination. These compositions do not add any thickness to the nail plate, nor can they cover or shield the plate surface from external injury, abuse or insult as do the polymerizable nail coatings described above. Nor do these compositions have any ability to fill in, reinforce or mask the longitudinal grooves of varying depth within the nail plate that are typical with advancing age.

Another commonly used nail hardening composition is based on dimethyl urea. Like methylene glycol compositions, dimethyl urea hardening compositions also penetrate the upper nail plate surface and cross-links with the proteins in keratin fibrils. Because dimethyl urea reactivity with proteins is lower that methylene glycol, cross-linking with keratin proteins occurs at a significantly slower rate. Nail hardening compositions containing dimethyl urea work in the same fashion as methylene glycol and also provide a significant increases in strength and surface hardness, at the cost of decreased flexibility of the nail plate. However, the slower reaction rates when compared to methylene glycol compositions translate into slower rates of increasing nail plate rigidity and require longer periods of continued applications before users notice any significant changes. The typical user often desires to achieve quick results and thus perceive the lower reactivity as a negative, which helps to explain why these compositions are not widely used in the marketplace. Also, as with methylene glycol compositions, these should not be used on already brittle or damaged nail plates.

Another commonly used type of nail hardening compositions are based on various types of natural extracts said to absorb and result in hardening of the upper surface of the nail plate, e.g. horsetail extract (Equisetum) or bamboo extract. Horsetail extract containing products are the most common example of a naturally derived extract, but even these enjoy only limited usage by consumers. Both extracts are said to contain high amounts of silica in the form of silicon dioxide (1-10%), which is claimed to cause nail plate hardening after repeated applications. These compositions usually require up to several applications per day for several weeks or more, but even then rarely provide any significant improvements in nail strength or durability. The nail plate provides an effective barrier against most substances unless penetrating agents are employed and even then does not readily absorb silicon dioxide. Because so little silicon dioxide can penetrate beyond even the first layers of the nail plate, compositions containing these extracts or other similar ingredients have very limited efficacy as a nail plate hardener nor do they have any significant ability to fill in and reinforce grooves that develop in the nail plate with advancing age. Natural oils such as avocado, jojoba, olive, etc. are sometimes applied and when absorbed can increase flexibility and reduce brittleness. These natural oils, however, are not useful on overly flexible nail plates. Natural oils do not protect the surface of the nail plate from external damage, nor can they provide any benefits for longitudinal ridges in the nail plate, and they must be applied repeatedly, often several times per day and continually on a daily basis to provide benefits These natural extract and/or oil compositions are substantially less efficacious as the other methods discussed herein. Natural extract compositions appeal to a certain small facet of the marketplace because they are often sold as "naturally-derived" and sometimes incorrectly as "all natural" nail hardening treatments. Natural oil compositions have wider appeal than those based on natural extracts, but are only effective for overly brittle nails. The natural oils do not provide the same degree of benefits for overly flexible nails, provide little to no benefit to prevent existing cracks or damage from worsening, and do not have any positive effect on longitudinal ridges in the nail plate and must be applied daily to have any long-term effectiveness, and are often perceived by users as being messy and inconvenient to use.

Another issue with the currently available nail treatment compositions is the difficulty in applying the compositions. Oftentimes, the composition must be applied daily or many times per times per day over an extended period of time.

It is therefore desirable to develop a nail plate strengthening composition that improves strength, toughness, durability, hardness and flexibility of the nail plate without causing embrittlement or other problems related to over hardening of the nail plate as described herein. It is also desirable to develop a nail strengthening composition that may be easy to apply, e.g., not require daily application, yet provide long-lasting strength and durability to any type of nail plate including those which are already brittle, weak, splitting, overly flexible or previously damaged. It is also desirable that such a composition protect the plate surface from externally damaging elements, e.g., excessive hand washing, use of cleaning agents, etc., as do compositions that rely on coating the surface of the nail with polymerizable mixtures, but without the disadvantage of substantially thickening the plate or requiring periodic removal which often results in plate roughening, thinning, weakening and increased cracking, splitting, pitting or peeling.

Therefore, a desirable composition would penetrate beneath the surface of the nail while still providing a thin, protective, cross-linked surface coating that will help prevent damage from externally applied forces or other damaging elements described above and would be permanent and not require periodic removal while remaining highly efficacious, nor would it allow the nail plate to become overly hard, lose flexibility, become embrittled, or require daily application. This composition would not only prevent nail plate weakening, cracking, splitting, delamination, etc., it would help to repair these types of preexisting nail damage and prevent worsening of these conditions, while maintaining a natural looking appearance. It would also be desirable for such compositions to have the ability to easily absorb or wick into cracks, splits and between delaminated layers of the nail plate to provide targeted repair to those areas which require additional reinforcement and thereby preventing worsening of these conditions, as well as to, fill-in, smooth over and reinforce longitudinal grooves found on the nail plate as a result of advancing age.

SUMMARY OF THE INVENTION

A first aspect of the present invention relates to a curable composition for strengthening and increasing durability of nail plates comprised of at least one polymerizable material, at least one penetrating agent, and at least one curing agent, and when required or deemed useful, a rheological thickening agent for controlling delivery, flow, placement and continuous coverage of the composition over the nail plate, while helping to prevent inadvertent skin contact with the curable composition.

A second aspect of the present invention relates to a curable composition for strengthening and increasing durability of nail plates is comprised of at least one polymerizable material, at least one curing agent and at least one penetrating agent which may also serve as a viscosity reducer to increase nail plate penetration and aid in wicking into crack fronts and other damaged areas, such as between separated nail plate layers, as demonstrated in cases of delaminating nail plates.

Another aspect of the present invention relates to a method for repairing and protecting damaged nail plates comprising of applying a curable composition to a nail plate, placing the nail plate under a heat source preferably for 1-5 min to promote penetration, removing excess polymerizable coating from the surface of the nail plate and then curing the applied composition under a fluorescent, cold cathode, laser or LED-style UV energy emitting device, as well as, incandescent, laser, LED (light emitting diode) or other types of visible light source, to include natural sources, that are suitable for use in such applications and repeating the application and curing of the composition as necessary to ensure the absorbed composition has cured into the nail plate to seal and repair any plate damage, as well as to form a smooth, continuous coating surface on the nail. The curable composition may comprise a polymerizable material, at least one penetrating agent, and at least one curing agent.

Yet another aspect of the present invention relates to a method for repairing and protecting damaged nail plates comprising of applying a curable composition to a nail plate, placing the nail plate under a heat source for time sufficient to promote improved penetration, such as, for example, 1 to 5 minutes, removing excess polymerizable coating from the surface of the nail plate and then curing the applied composition via free radical polymerization using catalyst or polymerization initiators suitable for use in such applications, and repeating the application and curing of the composition as necessary to ensure the cured composition has absorbed into the upper portions of the nail plate to seal and to assist in repairing any plate damage, as well as to form a smooth, continuous coating over the surface of the nail plate. The curable composition may comprise a polymerizable material, at least one polymerization enhancer and at least one curing agent.

A further aspect of the present invention relates to a curable composition comprised of at least one polymerizable material, at least one curing agent and at least one penetrating agent which may also serve as a viscosity reducer for purposes of wicking into cracks, splits or between delaminated layers of nail plate to provide targeted, localize adhesion to these areas for purposes of reinforcement and prevention of additional worsening of existing nail damage. Such a composition could also be used to provide spot treatment to areas which require additional reinforcement.

Another aspect of the present invention relates to a curable composition comprised of at least one polymerizable material and at least one curing agent and possibly at least one penetrating agent which may also serve as a viscosity reducer, as well as an opacifier or colorant for the purposes of providing either a complete coverage of the natural nail plate or wicking into cracks, splits, pits or between delaminated layers nail plate to provide targeted, localize adhesion and in both cases, to camouflage longitudinal grooves in the nail plate or areas of damage so they are less visible to the eye.

DETAILED DESCRIPTION

At least one embodiment of the present disclosure relates to a curable composition for strengthening and increasing toughness and durability of natural nail plates. As used herein, the term "strengthening" describes increasing or restoring toughness to the nail plate and increased durability so the nail plate can better endure impacts and resist externally physical forces in the form of everyday stresses and strains. "Toughness" describes a physical property synergistically achieved by the proper balance of strength and flexibility. "Hardness" is a surface property which describes resistance to scratching or indentation. "Flexibility" describes the ability of the coating to bend with the natural nail plate or the inherent flexibility of the natural nail plate when compared to brittle nails. "Durability" is a property inferred upon natural nail plates when they have sufficient toughness and surface hardness. A strengthening composition may be used to strengthen or protect an otherwise healthy nail, or may be used to repair, reconstruct, or toughen damaged or weak nails.

Penetration of the nail plate is difficult because the nail plate behaves as a highly selective barrier and prevents absorption of most substances, including most cosmetic and pharmaceutical ingredients. Since nail plate penetration is normally difficult, when absorption is made to occur, absorbed materials are restricted and limited to the upper one third portion of the natural nail plate. Penetration enhancers, or penetrating agents, described in this invention allow polymerizable material to migrate past the upper surface and concentrate in the upper portions of the nail, but the nail plate inherent barrier properties act to prevent deeper penetration into the nail plate. The proper selection of a penetrating agent allows for controlled deposition of the polymerizable material into the upper surface of the nail plate where it is most useful, while strictly limiting and/or likely preventing any penetration into deeper layers of the nail plate. Thus, the amount of penetration into the nail plate can be controlled by the choice of penetrating agent.

According to at least one embodiment, the curable composition may be comprised of a polymerizable material, at least one penetrating agent, and a curing agent.

The polymerizable material may comprise a reactive monomer or oligomer that is, under the conditions of use and as described herein, polymerizable within the nail plate. For example, polymerizable materials may include any methacrylate (methyl esters of methacrylic acid) including isomers, which contain mono, di, tri, tetra or penta reactive functional groups such as, but not limited to, hydroxyethyl methacrylate, hydroxypropyl methacrylate, butyl methacrylate, isobutyl methacrylate, t-butyl methacrylate, propyl methacrylate, hexyl methacrylate, cyclohexyl methacrylate di-HEMA trimethylhexyl dicarbamate, isobornyl methacrylate, ethoxyethyl methacrylate, 2-ethoxy ethoxy ethyl methacrylate, acetoacetoxythethyl methacrylate, ethyl methacrylate, methyl methacrylate, fluoro methacrylate, furfuryl methacrylate, ethylene dimethacrylate, 1,12-docecanediol dimethacrylate, diethylene glycol methyl ether methacrylate, triethylene glycol ethyl ether methacrylate, 1,3-butylene glycol dimethacrylate, 1,6-hexanediol dimethacrylate, glycerol methacrylate, sorbitol methacrylate, alkyl methacrylate, trimethylolpropane trimethacrylate, tetraethleyene glycol dimethacrylate, dipentaerythritol trimethacrylate, polyether methacrylate, ethylene glycol dimethacrylate, HEMA acetoacetate, isopropylidenephenyl bisoxyhydroxypropyl methacrylate, lauryl methacrylate, methoxydiglycol methacrylate, PEG-4 dimethacrylate, tetrahydrofurfuryl methacrylate, pyromelletic glycidyl dimethacrylate, triethylene glycol dimethacrylate, trimethylolpropane trimethacrylate, urethane methacrylate, diurethane methacrylate, urethane dimethacrylate, etc.

The polymerizable material may comprise a reactive monomer or oligomer that is, under the conditions of use and as described herein, polymerizable within the nail plate. For example, polymerizable materials may include any acrylate (methyl esters of acrylic acid) including isomers, which contain mono, di, tri, tetra or penta reactive functional groups such as, but not limited to analogs of the methacrylates described above and their isomers, e.g. 1,3-butylene glycol diacrylate, trimethylolpropane triacrylate, ethoxylated trimethylolpropane, triacrylate, pentaacrylate ester, dipentaerythritol pentaacrylate, urethane acrylate, diurethane acrylate, urethane diacrylate, etc.

The polymerizable material may also consist of dendrons and/or dendrimers, which are tree shaped molecules with a three-dimensional morphology and contain similar exposed reactive methacrylate and/or acrylate functional groups that under the conditions of use and as described herein, are polymerizable within the nail plate or for their more useful application nearly instant nail damage repair. By wicking deep between the delaminating layers of the nail plate or seeping into the tip of the crack-front, subsequent polymerization of absorbed materials in these zones halts crack front propagation and prevents further interlayer delamination of the nail plate and preventing further continuation and worsening of the existing damage. With the aid of a proper penetrating agent, migration into these microscopic spaces near a crack front is made possible for larger molecules such as dendrons, dendrimers and/or oligomers in concentrations that are useful. Other morphologies such as, cyclic, graft, comb or star geometries containing acrylate and/or methacrylate reactive functional groups are also useful for nail damage repair and can migrate into and deposit within areas of nail plate damage, when assisted by the proper use of an appropriate penetrating agent or synergistic blends penetrating agents.

The polymerizable material may be present in an amount ranging from about 40% to about 99%. In at least one embodiment, the polymerizable material is present in an amount ranging from about 60% to about 95%, and typical compositions range from about 60% to about 80%, or from 60% to about 70%.

In embodiments wherein the polymerizable material comprises larger molecules, such as dendrimers, dendrons, star polymers, or comb polymers, the larger molecules may comprise a small portion of the polymerizable material. For example, when the polymerizable material comprises a dendrimer, the dendrimer may be present in an amount less than 20%, such as for example, less than 10%, or less than 5%. According to at least one embodiment, the dendrimer may be present in an amount ranging from about 0.1 to about 10%, such as, for example, from about 0.5 to about 5%.

In at least one embodiment, the polymerizable material may be cured thermally or using ultraviolet A (UVA) wavelengths (400-315 nanometers) or those of the visible light spectrum, more specifically violet, blue, cyan, green (390-520 nanometers). The curing agent of the composition may comprise thermal accelerants or an UV or visible light photo initiator. Examples of thermal accelerants include aliphatic and aromatic amines, e.g., N,N-dimethyl-p-toluidine, N,N-dimethyl-1-phenylmethanamine, and N,N, dimethylbenzylamine.

Photoinitiators generate free radicals upon the absorption of UV light through one of two distinct mechanisms. Type I photoinitiators are compounds which undergo cleavage upon irradiation to generate two free radicals. The fragmentation may be a α-fragmentation, in which bond breakage occurs at a bond adjacent to the carbonyl group, or β-fragmentation, in which aromatic carbonyl compounds comprise substituents that facilitate direct photofragmentation. Benzoin and its derivatives are the most widely used Type I photoinitiators.

Type II photoinitiator systems comprise compounds that form an excited state upon irradiation and then abstract an atom or electron from a donor molecule, known as a synergist. The donor molecule then acts as the initiating species for polymerization. One commonly used Type II photoinitiator system comprises benzophenone as the photoinitiator and a tertiary amine as a synergist. Tertiary amines also serve to retard inhibition of polymerization by oxygen.

In at least one embodiment, the photoinitiator comprises at least one Type I photoinitiator, at least one Type II photoinitiator, or a combination of Type I and Type II photoinitiators. According to at least one embodiment, the photoinitiator comprises a combination of Type I and Type II photoinitiators.

Non-limiting examples of photoinitiators that may be used in accordance with the present disclosure include:
(benzene) tricarbonylchromium,
(cumene)cyclopentadienyliron(ii) hexafluorophosphate,
1,7-bis(9-acridinyl)heptane,
1-hydroxycyclohexyl phenyl ketone (Irgacure® 184),
2-(diethylamino)ethyl acrylate,
2-(diethylamino)ethyl methacrylate,
2-(dimethylamino)ethyl acrylate,
2,2',4-tris(2-chlorophenyl)-5-(3,4-dimethoxyp-enly)-4'5'-diphenyl-1,1'-biimidazole,
2,2'-bis(2-chlorophenyl)-4,4',5,5'-tetraphenyl-1,2'-bi-imidazole,
2,2-diethoxyacetophenone,
2,2-dimethoxy-2-phenylacetophenone (Irgacure® 651),
2,4-diethyl thioxanthone,
2,5-dimethylbenzophenone,
2-benzyl-2-(dimethylamino)-1-[4-(4-morpholinyl)phenyl]-1-butanone,
2-benzyl-2-(dimethylamino)-4'-morpholinobutyrophenone,
2-chlorothioxanthen-9-one,
2-dimethylamino-2-(4-methyl-benzyl)-1-(4-morpholin-4-ylphenyl)-butan-1-one,
2-ethyl hexyl-4-(dimethylamino)benzoate,
2-ethylanthraquinone,
2-hydroxy-1-[4-(hydroxyethoxy)phenyl]-2-methyl-1-propanone (Darocur® 2959)
2-hydroxy-2-methyl-1-phenyl-1-porpanone,
2-hydroxy-2-methylpropiophenone,
2-isopropyl thioxanthone,
2-methyl-1-[4-(methylthio)phenyl]-2-(4-morpholinyl)-1-propanone (Irgacure® 907),
2-methyl-4'-(methylthio)-2-morpholinopropiophenone,
2-methylbenzophenone,
3-(dimethylamino)propyl acrylate,
3,3',4,4'-benzophenonetetracarboxylic dianhydride,
3,4-dimethylbenzophenone,
3'-hydroxyacetophenone,
3-hydroxybenzophenone,
3-methylbenzophenone,
4-(2-hydroxyethoxy)phenyl(2-hydroxy-2-methylpropyl) ketone,
4-(4'-methylphenylthio)-benzophenone
4-(dimethylamino)benzophenone,
4,4'-bis(diethylamino)benzophenone,
4,4'-dihydroxybenzophenone,
4,4'-dimethylbenzil,
4-benzoylbiphenyl,
4-chloro benzophenone,
4'-ethoxyacetophenone,
4'-hydroxyacetophenone,
4-hydroxybenzophenone, 4-phenoxy-2.'2'-dichloro acetophenone,
4'-phenoxyacetophenone,
4-phenyl benzophenone,
acetophenone,
anisoin,
anthraquinone,
anthraquinone-2-sulfonic acid (sodium salt monohydrate),
benzil dimethyl ketal,
benzil,
benzoin ethyl ether,
benzoin isobutyl ether,
benzoin methyl ether,
benzoin,
benzophenone,
benzophenone/1-hydroxycyclohexyl phenyl ketone blend,
bisacryiphosphine oxide (Irgacure® 189),
butoxyethyl dimethylaminobenzoate,
camphorquinone,
dibenzosuberenone,
dimethylamino ethyl methacrylate,
diphenyl (2,4,6-trimethylbenzoyl)-phosphine oxide,
diphenyl(2,4,6-trimethylbenzoyl)phosphine oxide/2-hydroxy-2-methylpropiophenone blend,
ethyl 2,4,6-trimethylbenzoyldiphenyl phosphine oxide,
ethyl-4-(dimethylamino)benzoate,
ferrocene,
isoamyl 4-(dimethylamino)benzoate
methybenzoylformate,
methyl-2-benzoylbenzoate,
monoacryphosphine oxide (Darocur TPO),
n-phenyl glycine,
octyl-para-dimethylaminobenzoate,
phenanthrenequinone,
phenylpropanedione (Kanto PPD),
phosphine oxide, phenyl bis (2,4,6-trimethyl benzoyl),
isoamyl 4-(dimethylamino)benzoate
thioxanthen-9-one, and
triarylsulfonium hexafluoroantimonate salts.

UVA sensitive and/or visible light sensitive curing agent may be present in the composition in an amount sufficient to polymerize the reactive material to at least 90% degree conversion or cure within the first hour after beginning a thermal cure and within 5 minutes for UVA or visible light cure. For example, the curing agent may be present in an amount ranging from about 0.1% to about 5%, such as about 1%.

According to at least one embodiment, the polymerizable material does not cross-link with the keratin present within the nail when it is cured, only between polymerized chains of the polymerizable material.

In at least one embodiment, at least one penetrating agent comprises a material that enables the polymerizable material to penetrate the surface of the nail. For example, the penetrating agent may allow the polymerizable material to reach a depth of at least 0.05 mm beneath the surface of the nail. In other examples, the penetrating agent may allow the polymerizable material to reach a depth of at least 0.1 mm or at least 0.15 mm beneath the surface of the nail.

Penetrating agents in accordance with the present disclosure may comprise compounds chosen from oils and solvents. Any keratin penetrating agent known to those skilled in the art would also aid in the penetration of these polymerizable materials into the upper portions of the natural nail plate. The penetrating agent or blends of penetrating agents that may be present in the composition in an amount ranging, for example, from about 1% to about 40% by weight percent. In at least one embodiment, the penetrating agent is present in an amount ranging from about 5% to about 30%, such as, for example, from about 5% to about 20% or from about 10% to about 20%. According to other embodiments, the penetrating agent may be present in an amount less than about 5%, less than about 3%, less than about 2%, or less than about 1% by weight percent.

Non-limiting examples of natural oils which may be used singularly or in synergistic blends with other natural oils, their derivatives, include natural vegetable and plant oils such as; corn, castor, jojoba, olive, avocado, sweet almond, rice bran, sunflower, safflower, palm, palm kernel rapeseed, peanut, cottonseed, coconut, grape seed, tomato seed, hazelnut, soybean, tea tree, *eucalyptus*, wheat germ, sea buckthorn seed, argan, peppermint, macadamia, or others that may be obtained by expression, distillation, extraction of similar other means. Natural oils that are most suited to aid in absorption into the nail plate are those that most resemble oils which occur naturally in the nail plate and therefore have the greatest compatibility with the solid structural matrix that comprises the nail plate, therefore olive, jojoba and avocado are preferred.

Solvents which can increase penetration of polymerizable materials do so by lowering the viscosity of the composition and may be used with the natural oils or their derivatives listed above to lower viscosity and improve absorption of polymerizable materials. Some non-limiting examples of suitable solvents include acetone, ethyl alcohol, ethyl acetate, butyl acetate, amyl acetate, isopropyl alcohol, and methyl ethyl ketone, propylene glycol, octyldodecanol, glycerin, isodecane, cyclohexane, camphor, ethyl butyrolactone, butoxyethanol, butoxydiglycol, 2 octyldodecanol, diacetone alcohol, dichloromethane, dimethylsulfone, dimethyl isosorbide, diacetin, dipentene, toluene, xylene, triethylene glycol, triethylene glycol dimethacrylate, trimethylhexanol, tertrahydrofurfuryl acetate, turpentine, mineral spirits, etc.

In accordance with the present disclosure, the composition may further comprise at least one additional ingredient or additive. Such additives may include, for example, other solvents not used as penetrating agents, plasticizers, rheological agents, colorants or conditioning agents. In at least one embodiment, the natural oils used as penetrating agents also serve as plasticizers for both the polymerized material as well as for the nail plate itself, improving the flexibility of both simultaneously. Those skilled in the art could easily identify other migrating and non-migrating plasticizers which may also be employed, e.g. camphor. Plasticizers are additives that increase the plasticity or fluidity of a material such as polymer matrixes, ranging from synthetic plastics, including those made from acrylics, such as methacrylates, acrylates, cyanoacrylates and urethane acrylates to naturally occurring polymers such as keratin and cellulose. The properties of these materials are improved when blended with plasticizers, if these substances can embed themselves between the chains of polymers to increase the free volume between the polymer chains, thereby lowering the glass transition temperature, increasing flexibility, reducing hardness and/or improving durability. Commonly used plasticizers are from the chemical classes of sebacates, adipates, terephthalates, dibenzoates, gluterates, phthalates, azelates, glycols, polyethers and polycarboxylic acids with linear or branched aliphatic alcohols and blends of these. These compounds are selected on the basis of low toxicity, compatibility with the nail plate, formula composition and with the final polymerized material. The most preferred examples have low volatility and do not quickly escape from the resulting synthetic polymer or keratin via migration and evaporation. Phthalate esters of straight-chain and branched-chain alkyl alcohols are often used of which dibutyl phthalate is the most common example, however other phthalates are used, e.g. bis (2-ethylhexyl) phthalate. Trimellitates are often used for this purpose, e.g. trimethyl trimellitate and trimellitic anhydride are examples. Examples of adipate-based plasticizers are dioctyl adipate, dibutyl sebacate, dibutyl maleate and diisobutyl maleate. Other examples of plasticizers are dioctyl terephthalate, epoxidized vegetable oils, alkyl sulphonic acid phenyl ester, sulfonamides such as, toluene sulfonamide formaldehyde resin, N-ethyl toluene sulfonamide, N-(2-hydroxypropyl) benzene sulfonamide, glycols such as triethylene glycol dihexanoate, tetraethylene glycol diheptanoate, glycerides such as, acetylated monoglycerides, and alkyl citrates such as triethyl citrate, acetyl triethyl citrate, acetyl tributyl citrate, trioctyl citrate, acetyl trioctyl citrate, trihexyl citrate, acetyl trihexyl citrate, tributyl citrate and trimethyl citrate.

Further, polymerizable materials and curing processes described herein can also be used to create a polymerized matrix within the top portion of the natural nail plate which can serve as a carrier vehicle for substances which are active ingredients under Environmental Protection Agency (EPA) and Food and Drug Administration (FDA) regulations. For non-cosmetic related purposes, substances regulated as drug or pesticide, as are antimicrobial or antifungal agents, could be also be incorporated into these compositions and polymerized as described previously. The properties of the resultant polymer matrix can be adjusted and tailored to allow for controlled release of drug actives or other useful substances into the nail plate and surrounding areas. The resultant polymer matrix can alter the surface of the natural nail to have an increased or decreased hydrophobic or hydrophilic nature to facilitate or restrict migration into or through the nail plate, as well as to alter and control adhesion of any artificial nail coatings that may be subsequently applied, including nail polish and UV gel manicures. The resultant polymer matrix can significantly alter the surface hardness, scratch and dent resistances of the natural nail to provide increased resistance against scratch, denting, gouging, pitting or other forms of surface damage which can result from improper removal of any type of artificial nail coatings that may be subsequently applied, including nail polish and UV gel manicures or other types of normal abrasion encountered through daily living.

The compositions of the present disclosure may be devoid of methylene glycol or dimethyl urea, or any other compound that may cross-link with the keratin present in the nails.

The present invention further relates to methods of using the strengthening composition, such as methods for strengthening nails and methods for repairing nails.

At least one embodiment of the present disclosure relates to a method for strengthening nails comprising applying a curable composition to the nail. The curable composition may comprise a polymerizable material, at least one penetrating agent, and a curing agent. The curable composition may then be cured to polymerize the polymerizable material within the nail plate. In at least one embodiment, at least 95% of the polymerizable material is cured under the surface of the nail plate.

According to at least one embodiment, the steps of applying the composition and curing the composition may be repeated. For example, the steps of applying the composition and curing the composition may be repeated 2, 3, 4, 5, or more times depending on the initial condition of the nail and the desired level of strengthening.

In at least one embodiment, the composition may be applied at least two days in a row. In other embodiments, the composition may be applied as needed, such as weekly or biweekly, or any other interval based on the condition of the nail plate being treated.

In at least one embodiment, excess composition is wiped or blotted off or removed before curing. When the steps of applying the composition and curing the composition are repeated, excess composition may be wiped or blotted off before each curing step.

At least one embodiment of the present disclosure relates to a method for treating nails. As used herein, the term "treating" refers to repairing, restoring, or reconstructing the nail. The nail may be damaged, such as cracked, grooved, pitted, delaminated, peeled, or thinned due to physical abuse, such as removal of traditional nail enhancements, chemical exposure, illness, or the side-effect of medication or treatment.

In at least one embodiment, a curable composition may be applied to the nail, wherein the composition comprises a polymerizable material, at least one penetrating agent, and a curing agent. The applied composition may then be cured. The steps of applying and curing the composition may be repeated until the cured composition has covered and/or filled in the damaged area and formed a smooth surface on the nail plate.

When the damage is a crack, the cured composition may fill the crack such that the surface of the cured composition over the crack is continuous with the surface adjacent the crack. For grooved or ridged nails, the cured composition may level out the ridges by building up the lower surfaces of the nail to a level even with the tops of the ridges.

In at least one embodiment, the composition for treating the nail may comprise at least one penetrating agent, wherein the penetrating agent does not comprise a natural oil or plant oil.

In at least one embodiment, the penetrating agent may be chosen to penetrate the nail plate a desired amount. For example, when nails are cracked or grooved, it may be desirable to concentrate the treatment to the surface of the nail. In such a situation, the penetrating agent may be chosen from penetrating agents that do not allow the polymerizable material from penetrating the surface of the nail plate deeper than 0.1 mm, such as no deeper than 0.05 mm. In at least one embodiment, the penetrating agent is not present in the composition.

In at least one embodiment, excess composition is wiped or blotted off or removed before the composition is cured. For subsequent applications and curing of the composition, the excess composition may be wiped or blotted off after each application and before each curing step.

While the invention has been described in connection with specific embodiments thereof, it will be understood that those embodiments are exemplary only and this application is intended to cover any variations, uses, or adaptations of the invention following the principles of the invention and including such departures from the present disclosure as come within known or customary practice in the art and as follows in the scoped of the appended claims.

Unless otherwise specified, the percentages disclosed herein are based on weight.

EXAMPLES

Compositions

Samples 3-5, 3-10, and 3-30 were prepared using avocado oil, photo initiators, and HPMA.

|  | Sample 3-5 | Sample 3-10 | Sample 3-30 |
| --- | --- | --- | --- |
| Avocado Oil | 5% | 10% | 30% |
| Photo Initiators | 1% | 1% | 1% |
| HPMA | 94% | 89% | 69% |

In Samples 4-5, 4-10, and 4-30, the avocado oil in the above samples was replaced with rice bran oil.

|  | Sample 4-5 | Sample 4-10 | Sample 4-30 |
| --- | --- | --- | --- |
| Rice Bran Oil | 5% | 10% | 30% |
| Photo Initiators | 1% | 1% | 1% |
| HPMA | 94% | 89% | 69% |

Samples 5-5, 5-10, and 5-30 were prepared as above with sunflower oil as a penetrating agent.

|  | Sample 5-5 | Sample 5-10 | Sample 5-30 |
| --- | --- | --- | --- |
| Sunflower Oil | 5% | 10% | 30% |
| Photo Initiators | 1% | 1% | 1% |
| HPMA | 94% | 89% | 69% |

Samples 9-2.5, 9-5, and 9-10 were prepared using a combination of avocado oil and jojoba oil as the penetrating agent and HPMA and EDMA as the polymerizable material.

|  | Sample 9-2.5 | Sample 9-5 | Sample 9-10 |
| --- | --- | --- | --- |
| Avocado Oil | 1.25% | 2.5% | 5.0% |
| Jojoba Oil | 1.25% | 2.5% | 5.0% |
| HPMA | 90.5% | 88.0% | 80% |
| EDMA | 5.0% | 5.0% | 5.0% |
| 9559 Photoinitiator | 1.0% | 1.0% | 1.0% |
| Acetone | 1.0% | 1.0% | 1.0% |

The following samples were prepared with additional additives.

|  | Sample 008-12d-1a | Sample 008-12d-1b | Sample 008-12d-2a | Sample 008-12d-2b | 008-15d-1 V3.0 | 008-15d-2 V3.1 | 008-15d-3 V2.0 |
| --- | --- | --- | --- | --- | --- | --- | --- |
| Avocado Oil | 10.0% | 10.0% | 10.0% | 10.0% | 10.0% | 10.0% | 10.0% |
| Jojoba Oil | 10.0% | 10.0% | 10.0% | 10.0% | 10.0% | 10.0% | 10.0% |
| HPMA RM 9112-77 | 70% | 64% | 60.0% | 44.0% | 58.0% | 54.0% | 64.0% |
| EDMA RM 9054-26 | 5.0% | 5.0% | 5.0% | 5.0% | 7.5% | 7.5% | 5.0% |
| Photoinitiator RM 9559-5 | 1.0% | 1.0% | 1.0% | 1.0% | 1.0% | 1.0% | 1.0% |
| Acetone | 3.3% | 8.4% | — | — | 10.0% | 10.0% | 8.3% |
| Cellulose Acetate Butyrate CAB-381-0.5 | 0.7% | 1.7% | — | — | 4.0% | 8.0% | 1.7% |
| Urethane dimethacrylate silica concentrate 777-09 | — | — | 1.0% | 30.0 | — | — | — |

The following samples were prepared and cured with exposure to 2 minutes UV or 60 seconds LED light.

|  | Sample 008-17-4 V4.0 | Sample 008-17-5 V4.1 | Sample 008-19-1 V4.2 (Violet Tint) | Sample 008-19-3 SB5.3 | Sample 008-19-5 SB5.0 | Sample 008-19-6 SB5.1 |
| --- | --- | --- | --- | --- | --- | --- |
| Avocado Oil | 5.0% | 5.0% | 5.0% | 5.0% | — | 5.0% |
| Jojoba Oil | 5.0% | 5.0% | 5.0% | 5.0% | — | 5.0% |
| HPMA RM 9112-77 | 61.0% | 60.5% | 60.5% | 60.0% | 55.0% | 50.0% |
| EDMA RM 9054-26 | 10.0% | 10.0% | 10.0% | 9.0% | 9.0% | 9.0% |
| Photoinitiator RM 9559-5 | 1.0% | 1.0% | 1.0% | 1.0% | 1.0% | 1.0% |
| Ethyl Acetate | 10.0% | 10.0% | 10.0% | 20.0% | — | — |
| Cellulose Acetate Butyrate CAB-381-0.5 | 8.0% | 8.0% | 8.0% | — | — | — |
| Camphor | — | 0.5% | 0.5% | — | — | — |
| PMGDM in Acetone | — | — | — | — | 35.0% | 30.0% |

Sample 008-19-2 V4.3 was prepared by adding 0.24 parts by weight per 100 parts by weight of Sample 008-19-1 V4.2. Sample 008-19-2 V4.3 was cured by exposure to 2 minutes UV or 60 seconds LED light.

Sample 008-19-4 was prepared by adding 1.0 g cellulose acetate butyrate to 49.5 g Sample 008-19-3 SB5.3. Sample 008-19-4 was cured by exposure to 2 minutes UV or 60 seconds LED light.

The following samples were prepared and cured by exposure to 2 minutes UV or 60 seconds LED light.

|  | Sample 008-20-1 SB6.0 | Sample 008-20-2 SB6.1 | Sample 008-19-1 IB4.2 | Sample 008-20-3 IB7.0 | Sample 008-21-1 IB7.5 |
|---|---|---|---|---|---|
| Avocado Oil | — | — | 5.0% | 5.0% | 5.0% |
| Jojoba Oil | — | — | 5.0% | 5.0% | 5.0% |
| HPMA RM 9112-77 | 76.0% | 76.0% | 60.5% | 61.8% | 46.0% |
| Isobornyl methacrylate | — | — | — | — | 16.0% |
| EDMA RM 9054-26 | 13.0% | — | 10.0% | 8.7% | 8.7% |
| 50% PMGDM in trifunctional EDMA (triEDMA) | — | 13.0% | — | — | — |
| Photoinitiator RM 9559-5 | 1.3% | 1.3% | 1.0% | 1.0% | 1.0% |
| Ethyl Acetate | — | 10.0% | 10.0% | 10.0% | 10.0% |
| Cellulose Acetate Butyrate CAB-381-0.5 | — | — | 8.0% | 8.0% | 8.0% |
| Camphor | — | — | 0.5% | 0.5% | 0.5% |
| PMGDM in Acetone | 10.0% | — | — | — | — |
| D&C Violet | — | — | — | 6 ppm | 6 ppm |

Application
Spot Treatment

To spot treat damaged portions of the nail, the following procedure was followed.
  Any existing nail polish was removed and the nail was cleaned with a nail cleanser and dried with a lint free cloth.
  The composition was applied to the damaged portion of the nail (e.g., a delamination gap or crack) and allowed to wick into the damaged portion. Additional composition was added to the damaged portion until, the gap or crack was filled.
  The hand was placed under a heat lamp for 1 minute.
  Any excess composition that ran out of the damaged portion was carefully wiped away by avoiding pressure to the damaged portion. A cure of 4 minutes with the UV lamp or 2 minutes with LED was used to cure the composition.

Full Nail Application

The following procedure was used to apply a coating of the composition to the complete nail surface.
  Any existing nail polish was removed.
  The free-edge of all nails was shaped. Any delamination of the free edge and any excess free edge length was clipped off.
  The nails were cleaned with a nail cleanser.
  If the nails had delamination or damaged portions, a spot treatment was applied (see procedure above).
  The composition was gently shaken prior to each application.
  The composition was applied to the nail. According to this exemplary procedure, the composition was applied no closer to the soft tissue than 1/16" making sure to avoid all skin contact.
  The hand was placed under a heat lamp for 5 minutes.
  After the 5 minutes of heating, excess composition was removed by lightly wiping with a lint free pad. The composition was "capped" over the free-edge of the nail assuming there was enough free-edge to work with. Then the hand was placed in either a UV lamp for 2 minutes or an LED for 60 seconds. lamp.
  The application of the composition was repeated (as described above) with the exception that the hand was placed under the heat lamp for 3 minutes before curing the composition.

Test Subject #1

Compositions according to the present invention were applied to a test subject's (Test Subject #1) nails over a period of about 10 months. Test Subject #1 started the trial with severely damaged nails exhibiting splitting and peeling on both hands with a crack down the middle of one thumb nail.

Sample 008-12d-1a was applied to the nails approximately every 2 weeks for approximately 2 months. After 2 months, small remnants of the splitting remained and the crack on the thumbnail was visible, but could not be felt.

Sample 008-15d-2 was then applied to the nails approximately every week for 1 month. Only 3 nails exhibited splitting at the end of the month and the crack on the thumb nail had almost completely grown out.

Sample 008-17-4 was then applied to the nails approximately every 2 weeks for one month. Small amounts of delamination were still visible, but could not be felt. Test Subject #1 observed that her nails felt stronger and she was able to grow them longer.

Sample 008-19-5 (V4.2) was then used approximately every 2 weeks for 1 month. The nails remained sealed and Test Subject #1 observed that her nails continued to feel stronger.

Sample 008-20-3 (IB7.0) was then used approximately every week for 1 month with spot application of 008-20-2 (SB6.1) applied to delaminations. The nails remained sealed and the crack in the thumb nail was no longer present.

At the end of the trial, the nails of Test Subject #1 exhibited significantly improved strength and the delamination of the nails was sealed. The crack running the length of the thumbnail was sealed and grew out completely.

Test Subject #2

At the beginning of the trial, Test Subject #2 exhibited thin, weak, splitting and brittle nails. Test Subject #2 had used artificial nail coatings for at least 25 years, leaving her nails in a weakened state. Compositions according to the present invention were applied on a weekly or biweekly basis for a period of 10 months.

Application of Sample 008-12d-1b resulted in a reduction in the amount of jagged edges after 2 weeks of application.

Sample 008-15d-2 was applied approximately every 2 weeks for about 1 month.

The nails exhibited little delamination on a few fingers.

Sample 008-19-1 (V4.2) was applied weekly for approximately 1 month. The delamination was almost gone and the nails exhibited improved strength and growth.

At the end of the trial, Test Subject #2's nails exhibited a significant improvement in strength and reduction in delamination.

Test Subject #3

Test Subject #3 had been a user of shellac and her nails were very thin and tore easily without growing long. Both thumbs exhibited delamination. Compositions according to the present invention were applied weekly or biweekly over a period of about 9 months.

Samples 008-15d-2 (V3.1) and 008-15d-3 (V2.0) were applied to the left and right hand of Test Subject #3 for 7 consecutive weeks, altering the sample applied to each hand every week. Test Subject #3 observed that her nails felt smoother and stronger.

Sample 008-17-5 (V4.1) was then applied for 2 applications 2 weeks apart. At the start of the two weeks, the nails had been damaged and all had free edge wear and some had delamination. At the time of the second application, only 1 nail had delamination.

Sample 008-19-1 (V4.2) was applied every 1-2 weeks for approximately 3 months with spot treatment of the nails with Sample 008-20-2 (SB6.1). Ridges on the nails were smoother and the nails did not tear.

Sample 008-21-1 (IB7.5) was then used for weekly for approximately 2 months. Test Subject #3 observed that her nails were greatly improved and that her nails were able to grow long for the first time.

What is claimed is:

1. A method for treating nail plates comprising:
    a) applying a penetrating composition to at least a portion of the surface of a nail plate, wherein the composition comprises a polymerizable material, at least one penetrating enhancer and a curing agent;
    b) allowing the penetrating composition to penetrate the nail plate below the surface of the nail plate;
    c) removing excess of the penetrating composition from the surface of the nail plate; and
    d) curing the penetrating composition which has penetrated below the surface of the nail plate,
    wherein the polymerizable material is selected from the group consisting of hydroxyethyl methacrylate, hydroxypropyl methacrylate, butyl methacrylate, isobutyl methacrylate, t-butyl methacrylate, propyl methacrylate, hexyl methacrylate, cyclohexyl methacrylate, isobornyl methacrylate, ethoxyethyl methacrylate, 2-(ethoxyethoxy)ethyl methacrylate, acetoacetoxyethyl methacrylate, ethyl methacrylate, methyl methacrylate, fluoro methacrylate, furfuryl methacrylate, ethylene dimethacrylate, 1,12-docecanediol dimethacrylate, diethylene glycol methyl ether methacrylate, triethylene glycol ethyl ether methacrylate, 1,3-butylene glycol dimethacrylate, 1,6-hexanediol dimethacrylate, glycerol methacrylate, sorbitol methacrylate, alkyl methacrylate, trimethylolpropane trimethacrylate, tetraethlyene glycol dimethacrylate, dipentaerythritol trimethacrylate, polyether methacrylate, ethylene glycol dimethacrylate, HEMA acetoacetate, isopropylidenephenyl bisoxyhydroxypropyl methacrylate, lauryl methacrylate, methoxydiglycol methacrylate, PEG-4 dimethacrylate, tetrahydrofurfuryl methacrylate, pyromelletic glycidyl dimethacrylate, triethylene glycol dimethacrylate, trimethylolpropane trimethacrylate, urethane methacrylate, diurethane methacrylate, urethane dimethacrylate, bis(glyceryl dimethacrylate) pyromellitate and combinations thereof, and
    wherein step b) comprises placing the nail plate under a heat source.

2. The method of claim 1, further comprising repeating steps a)-d).

3. The method of claim 1, wherein step b) comprises allowing the penetrating composition to penetrate the nail plate to a depth of at least 0.05 mm below the surface of the nail plate.

4. The method of claim 1, wherein step b) comprises placing the nail plate under a heat source for 1 to 5 minutes.

5. The method of claim 1, wherein step c) comprises removing excess of the penetrating composition from the surface of the nail plate by at least one of wiping or blotting.

6. The method of claim 1, wherein the penetrating composition will not cross-link reactive functional groups of nail proteins.

7. The method of claim 1, wherein the curing agent includes at least one curing agent selected from the group consisting of ultraviolet (UV) and visible light photoinitiators.

8. The method of claim 1, wherein the at least one penetrating enhancer is present in the penetrating composition in an amount of from 5% to 30% by weight.

9. The method of claim 1, wherein the at least one penetrating enhancer includes at least one vegetable and/or plant oil, at least one solvent, or both at least one vegetable and/or plant oil and at least one solvent.

10. The method of claim 1, wherein the composition further comprises at least one additive selected from rheological agents, plasticizers, film forming agents, surface hardening agents, fillers, colorants, moisturizers, antimicrobial agents, antifungal agents, medicinal agents and active medical drugs.

11. The method of claim 1, wherein the at least one penetrating enhancer includes at least one penetrating agent selected from the group consisting of acetone, ethyl alcohol, ethyl acetate, butyl acetate, amyl acetate, isopropyl alcohol, methyl ethyl ketone, propylene glycol, octyldodecanol, glycerin, isodecane, cyclohexane, camphor, ethyl butyrolactone, butoxyethanol, butoxydiglycol, 2-octyldodecanol, diacetone alcohol, dichloromethane, dimethylsulfone, dimethyl isosorbide, diacetin, dipentene, toluene, xylene, triethylene glycol, trimethylhexanol, tetrahydrofurfuryl acetate, turpentine, and mineral spirits.

12. The method of claim 1, wherein the penetrating composition is applied to spot treat damaged portions of the nail plate.

13. The method of claim 1, wherein the penetrating composition is applied to the complete surface of the nail plate.

14. The method of claim 12, wherein damaged portions of the nail include peeling, free-edge cracks and pitting.

* * * * *